US007727195B2

(12) United States Patent
Norton

(10) Patent No.: US 7,727,195 B2
(45) Date of Patent: Jun. 1, 2010

(54) SYRINGE DEVICE HAVING VENTING SYSTEM

(75) Inventor: Paul H. Norton, Trumbauersville, PA (US)

(73) Assignee: West Pharmaceutical Services, Inc., Lionville, PA (US)

( * ) Notice: Subject to any disclaimer, the term of this patent is extended or adjusted under 35 U.S.C. 154(b) by 14 days.

(21) Appl. No.: 11/169,345

(22) Filed: Jun. 29, 2005

(65) Prior Publication Data

US 2006/0116644 A1    Jun. 1, 2006

Related U.S. Application Data

(60) Provisional application No. 60/584,893, filed on Jul. 1, 2004.

(51) Int. Cl.
*A61M 1/00* (2006.01)

(52) U.S. Cl. .................. 604/122; 604/124; 604/126; 604/199; 604/218

(58) Field of Classification Search .................. 604/181, 604/187, 218, 122, 126, 190, 199, 124, 125
See application file for complete search history.

(56) References Cited

U.S. PATENT DOCUMENTS

| 4,030,498 | A |   | 6/1977  | Tompkins       |         |
|-----------|---|---|---------|----------------|---------|
| 4,424,817 | A | * | 1/1984  | Williams       | 600/579 |
| 4,466,446 | A |   | 8/1984  | Baidwan et al. |         |
| 4,690,154 | A |   | 9/1987  | Woodford et al.|         |
| 4,973,308 | A |   | 11/1990 | Borras et al.  |         |
| 5,045,065 | A |   | 9/1991  | Raulerson      |         |
| 5,180,370 | A | * | 1/1993  | Gillespie      | 604/110 |

(Continued)

FOREIGN PATENT DOCUMENTS

EP    0945150 A2    9/1999

(Continued)

OTHER PUBLICATIONS

International Search Report and Written Opinion of the International Searching Authority mailed Sep. 26, 2006 for related International Application No. PCT/US05/23754.

(Continued)

*Primary Examiner*—Kevin C Sirmons
*Assistant Examiner*—Bhisma Mehta
(74) *Attorney, Agent, or Firm*—Panitch Schwarze Belisario & Nadel LLP

(57) ABSTRACT

A syringe device includes a syringe tube having a distal end with a passageway in fluid communication with a cavity thereof. A plunger rod slidingly and sealingly engages within the cavity of the syringe tube. The plunger rod includes at least one aperture in fluid communication with a hollow interior of the plunger rod. A plunger tip is engaged with a distal end of the plunger rod and interacts with an inner surface of the side wall of the syringe tube to separate the cavity into first and second areas. The at least one aperture fluidly connects the hollow interior of the plunger rod and the first area of the syringe tube cavity, such that the generally hollow plunger rod interior allows air to move between an outside of the syringe device and the first area of the cavity during sliding movement of the plunger rod within the syringe tube.

7 Claims, 2 Drawing Sheets

U.S. PATENT DOCUMENTS

| | | | |
|---|---|---|---|
| 5,238,003 A | | 8/1993 | Baidwan et al. |
| 5,374,401 A | * | 12/1994 | von Berg .................... 422/101 |
| 5,599,312 A | | 2/1997 | Higashikawa |
| 5,865,803 A | | 2/1999 | Major |
| 6,086,559 A | | 7/2000 | Enk |
| 6,139,530 A | * | 10/2000 | Hiejima et al. ............. 604/140 |
| 6,440,101 B1 | * | 8/2002 | Grabenkort et al. ........... 604/89 |
| 6,572,584 B1 | * | 6/2003 | Shaw et al. ................. 604/110 |
| 2005/0101920 A1 | | 5/2005 | Keane et al. |

FOREIGN PATENT DOCUMENTS

| | | | |
|---|---|---|---|
| EP | 1530978 A1 | * | 5/2005 |
| JP | 2004097640 A | * | 4/2004 |
| WO | 2006/007592 A2 | | 1/2006 |

OTHER PUBLICATIONS

Second Office Action dated Mar. 20, 2009 for related Chinese Appl. 200580022388.4.

First Office Action dated Aug. 22, 2008 for related Chinese Appl. 200580022388.4.

\* cited by examiner

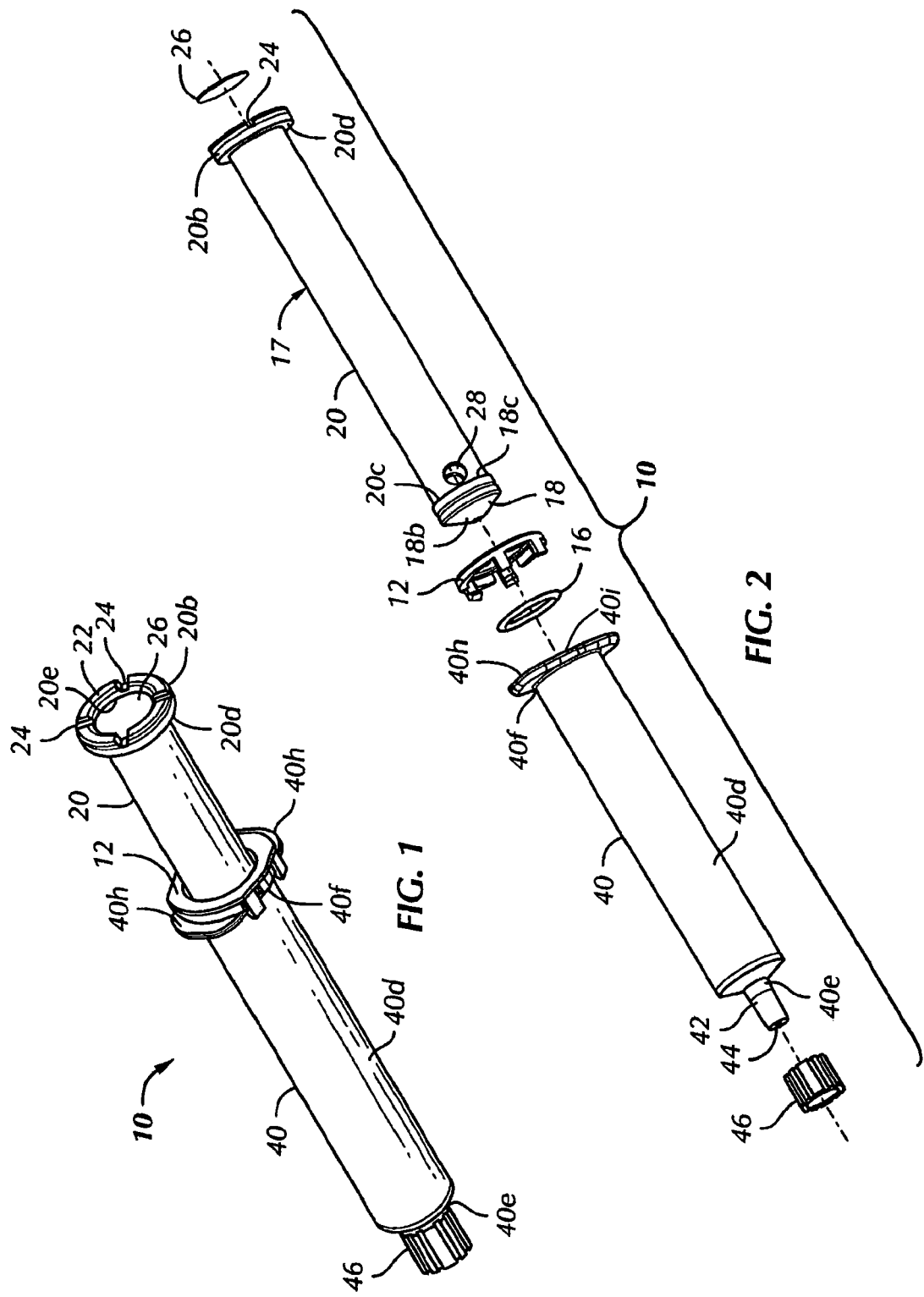

SYRINGE DEVICE HAVING VENTING SYSTEM

CROSS-REFERENCE TO RELATED APPLICATIONS

This patent application claims priority to U.S. Provisional Patent Application No. 60/584,893, filed Jul. 1, 2004, entitled "Syringe Device Having Venting System", the disclosure of which is incorporated herein by reference.

BACKGROUND OF THE INVENTION

This invention generally relates to syringe devices and, more particularly, to a venting system for use with a syringe device that operates to lessen the likelihood of contamination of contents of the syringe device.

It is often desirable to store drugs in a concentrated or powdered form until just prior to administering the drug to a patient, at which time, the medicine is mixed with a solvent, diluent or rehydrant in a reconstitution process. Typically, a solvent from a syringe device is injected into a container containing the concentrated drug. Upon completion of the reconstitution process, the reconstituted drug is drawn from the container into the syringe device and then subsequently administered to a patient using the syringe device.

The syringe devices of the prior art typically have no seal between a plunger rod and an end of the syringe tube in which the plunger rod is inserted. It is because of this lack of a seal in conventional syringe devices that potentially contaminated air is able to access an upper area of the syringe tube during the reconstitution process, thereby potentially contaminating an interior wall of the syringe tube. When the mixture is drawn back into the syringe tube, the mixture comes into contact with the interior wall of the syringe tube, thereby potentially becoming contaminated. Some drugs take longer to dissolve than others, resulting in increased reconstitution process durations and an increased possibility of contamination.

It would therefore be desirable to have a syringe device for use in a reconstitution processes that inhibits contaminated air from entering a syringe tube to lessen the likelihood that the medicine mixture drawn back into the syringe tube will become contaminated.

BRIEF SUMMARY OF THE INVENTION

Briefly stated, the present invention is a syringe device for administering a medicament. The syringe device comprises a syringe tube having a side wall, a distal end, and a proximal end defining a cavity within the syringe tube for containing the medicament. The distal end has a passageway in fluid communication with the cavity. A plunger rod sealingly engages with the syringe tube. The plunger rod is slidingly disposed at least partially within the cavity of the syringe tube. The plunger rod has a distal end, a generally hollow interior, and a generally open proximal end. The plunger rod includes at least one aperture in fluid communication with the hollow interior of the plunger rod. A plunger tip is engaged with the distal end of the plunger rod and is slidable therewith within the cavity. The plunger tip sealingly interacts with an inner surface of the side wall of the syringe tube to separate the cavity into first and second areas. The first area is disposed between the plunger tip and the proximal end of the syringe tube. The second area is disposed between the plunger tip and the distal end of the syringe tube. The at least one aperture fluidly connects the hollow interior of the plunger rod and the first area of the cavity of the syringe tube, such that the generally hollow interior of the plunger rod allows air to move between an outside of the syringe device and the first area of the cavity during sliding movement of the plunger rod within the syringe tube.

In another aspect, the present invention is in a plunger for use with a syringe tube having a side wall, a distal end, and a proximal end defining a cavity within the syringe tube for containing a medicament. The distal end has a passageway in fluid communication with the cavity. The plunger comprises a plunger rod sealingly engaged with the syringe tube. The plunger rod is slidingly disposed at least partially within the cavity of the syringe tube. The plunger rod has a distal end, a generally hollow interior, and a generally open proximal end. The plunger rod includes at least one aperture in fluid communication with the hollow interior of the plunger rod. A plunger tip is engaged with the distal end of the plunger rod and is slidable therewith within the cavity. The plunger tip sealingly interacts with an inner surface of the side wall of the syringe tube to separate the cavity into first and second areas. The first area is disposed between the plunger tip and the proximal end of the syringe tube. The second area is disposed between the plunger tip and the distal end of the syringe tube. The at least one aperture fluidly connects the hollow interior of the plunger rod and the first area of the cavity of the syringe tube, such that the generally hollow interior of the plunger rod allows air to move between an outside of the syringe tube and the first area of the cavity during sliding movement of the plunger rod within the syringe tube.

BRIEF DESCRIPTION OF THE SEVERAL VIEWS OF THE DRAWINGS

The foregoing summary, as well as the following detailed description of a preferred embodiment of the invention, will be better understood when read in conjunction with the appended drawings. For the purpose of illustrating the invention, there is shown in the drawings an embodiment which is presently preferred. It should be understood, however, that the invention is not limited to the precise arrangements and instrumentalities shown.

In the drawings:

FIG. 1 is a side rear perspective view of a syringe device having a vented plunger rod in accordance with a preferred embodiment of the present invention;

FIG. 2 is an exploded perspective view of the syringe device of FIG. 1;

DETAILED DESCRIPTION OF THE INVENTION

Figure 3:
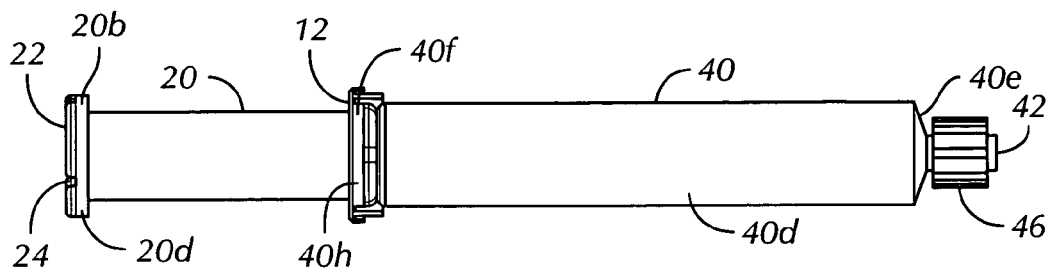
FIG. 3 is a side elevational view of the syringe device of FIG. 1.

Certain terminology is used in the following description for convenience only and is not limiting. The words "right," "left," "upper," and "lower" designate directions in the drawings to which reference is made. The terminology includes the words above specifically mentioned, derivatives thereof, and words of similar import.

Referring to the drawings in detail, wherein like numerals indicate like elements throughout, there is shown in FIGS. 1-5 a preferred embodiment of a syringe device, indicated generally at 10, for administering a medicament (not shown), the syringe device 10 having a venting system in accordance with the present invention. Preferably, the venting system of the syringe device 10 is a plunger 17 including a vented plunger rod 20.

Referring to FIGS. 1-5, the syringe device 10 comprises the generally hollow plunger rod 20 slidingly disposed at least partially within a cavity 40g of the syringe tube 40. The syringe tube 40 has a side wall 40d, a distal end 40e, and a proximal end 40f having an opening 40i defining the cavity 40g within the syringe tube 40 for containing the medicament. The distal end 40e preferably has a nozzle 42 extending generally axially therefrom with a passageway 44 therethrough in fluid communication with the cavity 40g of the syringe tube 40. Preferably, a collar 46 is affixed to the nozzle 42 to enable a needle (not shown) or other such device to be removably engaged to the nozzle 42 during use of the syringe device 10. It is preferred that the collar 46 is a luer lock or other such retaining device, although this is not intended to be limiting, as it is within the spirit and scope of the present invention that the collar 46 be any retaining device capable of retaining the needle or other similar device on the nozzle 42.

Preferably, the plunger rod 20 is sealingly engaged with the syringe tube 40. The plunger rod 20 preferably is generally cylindrical and has a generally hollow interior 20a, a distal end 20c, and a generally open proximal end 20b. The plunger rod 20 includes at least one aperture 28 in fluid communication with the hollow interior 20a of the plunger rod 20. It is preferable that the at least one aperture 28 be disposed proximate the distal end 20c of the plunger rod 20, although it is within the spirit and scope of the present invention that the at least one aperture 28 be located at any location along the plunger rod 20, provided the at least one aperture 28 remains within the cavity 40g of the syringe tube 40 during a desired range of motion of the plunger rod 20. Additionally, it is preferable that there be two apertures 28, preferably diametrically opposed and disposed proximate the distal end 20c of the plunger rod 20. Although this configuration is preferred, it is within the spirit and scope of the present invention that there be more or less than two apertures 28 or that the apertures 28 be spaced differently, such as, but not limited to, side-by-side or unevenly spaced about the circumference of the plunger rod 20.

Figure 4:
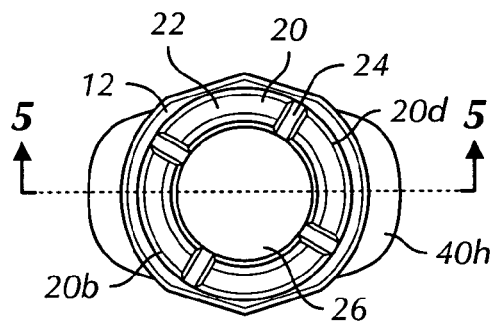
FIG. 4 is a rear elevational view of the syringe device of FIG. 1.

Referring now to FIGS. 1, 2, and 4, the proximal end 20b of the plunger rod 20 preferably has an opening 20e therein. Preferably, a filter 26 is disposed within the proximal end 20b of the plunger rod 20 through which air passes during sliding movement of the plunger rod 20 within the syringe tube 40. It is preferred that the filter 26 extends completely across the opening 20e in the proximal end 20b of the plunger rod 20. Preferably, the filter 26 is a microbial filter 26 for removing at least some contaminants from the air.

Referring to FIGS. 1 and 4, extending radially outwardly from the proximal end 20b of the plunger rod 20 is a generally annular flange 20d. The flange 20d preferably includes a face or raised portion 22 extending axially outwardly from the flange 20d. The raised portion 22 includes at least one radial groove 24 therein. Preferably, the raised portion 22 includes four evenly spaced grooves 24 extending radially therethrough. Although it is preferred that there be four evenly spaced grooves 24, it is within the spirit and scope of the present invention that there be more or less than four grooves 24 and that they be unevenly spaced. Although not portrayed in the figures, it is contemplated that a generally rigid piece of material (not shown) be attached to the proximal end 20b of the plunger rod 20, preferably bonded to the raised portion 22 using adhesive, thermal welding, or sonic welding, to name a few, in order to at least partially cover the filter 26 while leaving the at least one groove 24 generally unobstructed. In this way, the piece of material acts to at least partially protect the filter 26 from damage, such as, but not limited to, tearing or puncturing during use or storage of the syringe device 10.

Figure 5:
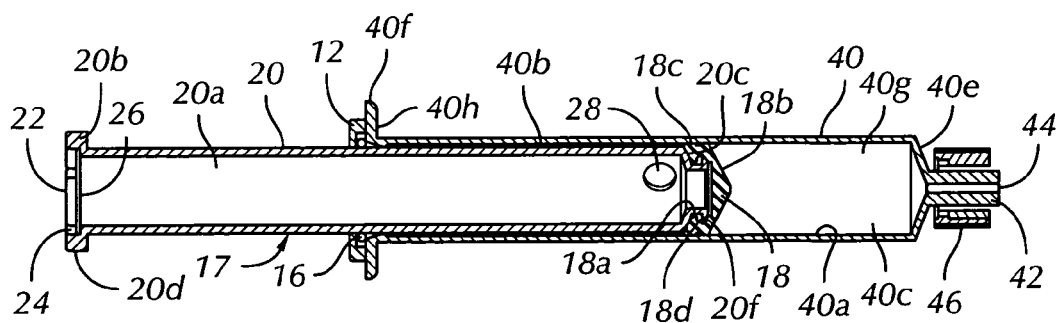
FIG. 5 is a cross-sectional view of the syringe device of FIG. 4 taken along line 5—5.

Referring now to FIGS. 2 and 5, preferably, a plunger tip 18 is engaged with the distal end 20c of the plunger rod 20 and is slidable therewith within the cavity 40g throughout a desired range of motion. The plunger tip 18 is preferably made from an elastomeric material such as rubber. Preferably, the plunger tip 18 is generally cylindrical in shape, having a generally conical distal end 18b, and sized so as to fit snugly within the syringe tube 40. Preferably, the plunger tip 18 is in constant direct sealing engagement and sealingly interacts with an inner surface 40a of the side wall 40d of the syringe tube 40 to separate the cavity 40g into first and second areas 40b, 40c as the plunger tip 18 slides throughout the desired range of motion, as will be described in more detail below. The plunger tip 18 preferably has a circular cavity 18a centrally disposed in a proximal end 18c and extending a distance into the plunger tip 18. The cavity 18a is preferably shaped to frictionally engage the distal end 20c of the plunger rod 20 so that the plunger tip 18 moves with the plunger rod 20, thereby forming the plunger 17. Specifically, it is preferred that the distal end 20c of the plunger rod 20 have a radially extending nib 20f which engages within an annular recess 18d within the cavity 18a of the plunger tip 18. Although this configuration is preferred, it is within the spirit and scope of the present invention that the plunger tip 18 be retained on the distal end 20c of the plunger rod 18 in a different manner, such as, but not limited to, threadably engaging the plunger tip 18 onto the distal end 20c of the plunger rod 18.

As discussed above, it is preferred that the at least one aperture 28 is disposed through the plunger rod 20 proximate the distal end 20c, preferably close to the proximal end 18c of the plunger tip 18. Although this location is preferred, it is within the spirit and scope of the present invention that the at least one aperture 28 be disposed in any portion of the plunger rod 20 that does not come into direct contact with outside air during a reconstitution process. b2

Referring specifically to FIG. 5, the plunger rod 20 and the plunger tip 18 are slidable within the syringe tube 40 such that the plunger tip 18 creates a moveable seal with the inner surface 40a of the syringe tube 40 to divide the syringe tube 40 into the first and second areas 40b, 40c. The first area 40b of the cavity 40 of the syringe tube 40 is disposed between the plunger tip 18 and the proximal end 40f of the syringe tube 40, and the second area 40c is disposed between the plunger tip 18 and the distal end 40e of the syringe tube 40. In other words, the first area 40b (or a first cavity 40b) is defined between the seal 16 and the plunger tip 18 and between the syringe tube 40 and the plunger rod 20. In this way, the plunger tip 18 allows for the pushing of liquid (not shown) out of or the drawing of a mixture (not shown) into the second area 40c between the plunger tip 18 and the distal end 40e of the syringe tube 40 while not allowing any of the liquid or mixture into the first area 40b between the plunger tip 18 and the proximal end 40f of the syringe tube 40. The at least one aperture 28 fluidly connects the hollow interior 20a of the plunger rod 20 and the first area 40b of the cavity 40g of the syringe tube 40, such that the generally hollow interior 20a of the plunger rod 20 allows air to move between outside of the syringe device 10 and the first area 40b of the cavity 40g during sliding movement of the plunger rod 20 within the syringe tube 40. In other words, the first cavity 40b is vented to an exterior of the syringe device 10 through a flowpath including the at least one aperture 28, the hollow interior of the plunger rod 20 and the filter 26.

Referring to FIGS. 1, 2, 4, and 5, a radially extending generally ovular flange 40h is preferably positioned at or near the proximal end 40f of the syringe tube 40 to provide a surface for a user to grip the syringe tube 40 during use of the syringe device 10. A connection member 12 is preferably engaged with the proximal end 40f of the syringe tube 40 to essentially cap the proximal end 40f of the syringe tube 40. While the connection member 12 is portrayed in the figures as clipping onto the proximal end 40f of the syringe tube 40, it is within the spirit and scope of the present invention that the connection member 12 be attached to the proximal end 40f of the syringe tube 40 in other ways, provided the connection member 12 still functions in the manner described below. For instance, attachment can be accomplished by bonding the connection member 12 to the proximal end 40f of the syringe tube 40 using adhesive, thermal welding, or sonic welding, to name a few. b3

The connection member 12 preferably has a hole through a top surface through which the plunger rod 20 passes. Preferably, the connection member 12 functions to retain a seal 16 disposed between the syringe tube 40 and the plunger rod 20 at or near the proximal end 40f of the syringe tube 40 for sealingly engaging the plunger rod 20 and the syringe tube 40 to inhibit air from passing into the first area 40b of the cavity 40g of the syringe tube 40 between the plunger rod 20 and the proximal end 40f of the syringe tube 40. That is, the seal 16 is supported by the syringe tube 40 proximate the opening 40i at the proximal end of the syringe tube 40 in slidable sealing engagement with the plunger rod 20 and inhibits outside air from directly entering and exiting the first area 40b of the syringe tube 40. The seal 16 is preferably an elastomeric O-ring seal 16. Although only the connection member 12 is described above as retaining the seal 16 within the proximal end 40f of the syringe tube 40, it is within the spirit and scope of the present invention that additional structures be used in conjunction with or instead of the connection member 12. For instance, it is contemplated that a separate sleeve (not shown) be used to wrap around the proximal end 40f of the syringe tube 40 and the connection member 12, thereby helping to retain the seal 16 within the proximal end 40f of the syringe tube 40. Such a configuration is described and portrayed in U.S. Provisional Patent Application No. 60/584,893, the disclosure of which is incorporated herein by reference.

Preferably, the plunger rod 20, the syringe tube 40, and the connection member 12 are made of a polymeric material, although it is within the spirit and scope of the present invention that these components be made of different materials, such as glass or metal, for instance.

In operation, the syringe device 10 contains a liquid (not shown), such as a saline solution, in the second area 40c of the syringe tube 40 between the plunger tip 18 and the distal end 40e of the syringe tube 40. The distal end 40e of the syringe tube 40 is then engaged with a container (not shown) containing a powdered medicinal product (not shown). Preferably, a needle (not shown) is engaged to the nozzle 42 using the collar 46 to retain the needle thereon. The needle can then be used to engage the syringe device 10 with the container and provide a fluid connection therebetween. The user then injects the liquid from the second area 40c of the syringe tube 40 into the container to mix with and dissolve the powder therein by placing a thumb on the raised portion 22 of the flange 20d (or, alternatively, on the piece of material (not shown) at least partially covering the filter 26, as described above) of the plunger rod 20 and at least one finger on each side of the flange 40h of the syringe tube 40 and pushing down the plunger rod 20, consequently moving the plunger tip 18 distally through the interior of the syringe tube 40 and forcing the liquid out of the second area 40c through the passageway 44 of the nozzle 42. While the plunger rod 20 is being pushed distally into the syringe tube 40, air enters the generally hollow interior 20a of the plunger rod 18 through the microbial filter 26 across the opening 20e at the proximal end 20b of the plunger rod 20 and passes through the at least one aperture 28 to enter the first area 40b of the cavity 40g of the syringe tube 40 to fill the increasing volume thereof. The air is able to flow around the user's thumb (or around the piece of material at least partially covering the filter 26), which is necessarily placed across the raised portion 22 of the flange 20d of the plunger rod 20 and likely covering at least the majority of the opening 20e at the proximal end 20b of the plunger rod 20, and access the interior 20a of the plunger rod 20 by passing through the grooves 24 in the raised portion 22 of the flange 20d of the plunger rod 20. By passing through the microbial filter 26, at least some of the contaminants are removed from the air to lessen the likelihood of contamination of the interior surface 40a of the syringe tube 40. Once the medicinal powder is adequately dissolved in the liquid, the mixture is drawn from the container and into the second area 40c of the syringe tube 40 by pulling the plunger rod 20 proximally (axially outwardly from the proximal end 40f of the syringe tube 40). The air contained in the first area 40b is allowed to escape the syringe device 10 by passing through the at least one aperture 28 and out of the opening 20e, through the microbial filter 26, at the proximal end 20b of the plunger rod 20. The mixture within the syringe device 10 can now be injected using the syringe device 10. The user may optionally remove the needle used for engaging the syringe device 10 with the container and replace it with another needle (not shown) to use for the injection.

The syringe device 10 of the present invention seals the first area 40b of the syringe tube 40 and only allows controlled access thereto of ambient air. That is, the air must pass through microbial filter 26 before entering the first area 40b. In this way, the syringe device 10 lessens the likelihood that a mixture drawn back into the syringe tube 40 will become contaminated.

Although only the vented plunger rod 20 is described above, it is within the spirit and scope of the present invention that other venting systems be used with the syringe device 10 of the present invention. For instance, the venting system could take the form of a vent in the syringe tube 40, preferably proximate the connection member 12 at the proximal end 40f of the syringe tube 40 (not shown). Alternatively, a vent could be disposed between the syringe tube 40 and the plunger rod 20 (not shown). For each above-stated alternative venting system, it would be preferable that there be a microbial filter disposed across the vent in order to remove at least some contaminants from the ambient air to lessen the likelihood that a mixture drawn back into the syringe tube 40 will become contaminated.

Furthermore, although only the use of the syringe device 10 for reconstitution is described above, it is not intended to be limiting. Therefore, it is within the spirit and scope of the present invention that the syringe device 10 be used in other applications in which it would be desirable to lessen the likelihood of contaminating the inside of a syringe tube and the contents therein, such as disposable single-use syringes, pre-filled syringes used to mix two liquids together, and the like.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention.

I claim:

1. A syringe device for administering a medicament, comprising:
a syringe tube having a side wall, a distal end, and a proximal end defining a cavity within the syringe tube for containing the medicament, the distal end having a passageway in fluid communication with the cavity;
a plunger rod sealingly engaged with the syringe tube, the plunger rod being slidingly disposed at least partially within the cavity of the syringe tube, the plunger rod having a distal end, a generally hollow interior, and a generally open proximal end, the plunger rod including at least one aperture in fluid communication with the hollow interior of the plunger rod; and
a plunger tip engaged with the distal end of the plunger rod and configured to slide within the cavity throughout a range of motion, the plunger tip in constant direct sealing engagement with an inner surface of the side wall of the syringe tube to separate the cavity into first and second areas as the plunger tip slides throughout the range of motion, the first area disposed between the plunger tip and the proximal end of the syringed tube and the second area disposed between the plunger tip and the distal end of the syringe tube, the at least one aperture fluidly connecting the hollow interior of the plunger rod and the first area of the cavity of the syringe tube, such that the generally hollow interior of the plunger rod allows air to move between an outside of the syringe device and the first area of the cavity during sliding movement of the plunger rod within the syringe tube.

2. The syringe device of claim 1, wherein the filter is a microbial filter for removing at least some contaminants from the air.

3. The syringe device of claim 1, further comprising a seal disposed between the syringe tube and the plunger rod proximate the proximal end of the syringe tube for sealingly engaging the plunger rod and the syringe tube to inhibit air from passing into the first area of the cavity of the syringe tube between the plunger rod and the proximal end of the syringe tube.

4. The syringe device of claim 1, wherein the at least one aperture comprises two diametrically opposed apertures.

5. The syringe device of claim 1, wherein the at least one aperture is proximate the distal end of the plunger rod.

6. The syringe device of claim 1, wherein the proximal end of the plunger rod includes a flange extending radially outwardly therefrom, the flange including a raised portion extending axially outwardly from the flange, the raised portion including at least one radial groove therein.

7. A syringe device for administering a medicament comprising:
a syringe tube having a side wall, a distal end, and a proximal end defining a cavity within the syringe tube for containing the medicament, the distal end having a passageway in fluid communication with the cavity, and the proximal end having an opening;
a plunger rod configured to slide within the cavity of the syringe tube throughout a desired range of motion, the plunger rod having:
a distal end,
a proximal end,
a generally hollow interior, and
an opening proximate the proximal end of the plunger rod in fluid communication with the hollow interior;
a filter disposed in the opening proximate the proximal end of the plunger rod;
a plunger tip engaged with the distal end of the plunger rod and slidable therewith within the cavity, the plunger tip in constant direct sealing engagement with an inner surface of the side wall of the syringe tube;
a seal supported by the syringe tube proximate the opening at the proximal end of the syringe tube, the seal being in slidable sealing engagement with the plunger rod;
a first cavity defined between the seal and the plunger tip and between the syringe tube and the plunger rod; and
at least one aperture in the plunger rod in fluid communication with the hollow interior of the plunger rod and the first cavity,
wherein during sliding movement of the plunger rod within the syringe tube, the first cavity is vented to an exterior of the syringe device through a flowpath including the at least one aperture, the hollow interior of the plunger rod and the filter.

* * * * *

UNITED STATES PATENT AND TRADEMARK OFFICE
CERTIFICATE OF CORRECTION

PATENT NO. : 7,727,195 B2
APPLICATION NO. : 11/169345
DATED : June 1, 2010
INVENTOR(S) : Paul H. Norton It is certified that error appears in the above-identified patent and that said Letters Patent is hereby corrected as shown below:

In the Claims

Column 7, Line 6-34, Claim 1 should read:

1. A syringe device for administering a medicament, comprising:

a syringe tube having a side wall, a distal end, and a proximal end defining a cavity within the syringe tube for containing the medicament, the distal end having a passageway in fluid communication with the cavity;

a plunger rod sealingly engaged with the syringe tube, the plunger rod being slidingly disposed at least partially within the cavity of the syringe tube, the plunger rod having a distal end, a generally hollow interior, and a generally open proximal end, the plunger rod including at least one aperture in fluid communication with the hollow interior of the plunger rod and a filter disposed within the proximal end of the plunger rod; and a plunger tip engaged with the distal end of the plunger rod and configured to slide within the cavity throughout a desired range of motion, the plunger tip in constant direct sealing engagement with an inner surface of the side wall of the syringe tube to separate the cavity into first and second areas as the plunger tip slides throughout the desired range of motion, the first area disposed between the plunger tip and the proximal end of the syringe tube and the second area disposed between the plunger tip and the distal end of the syringe tube, the at least one aperture fluidly connecting the hollow interior of the plunger rod and the first area of the cavity of the syringe tube, such that the generally hollow interior of the plunger rod allows air to move between an outside of the syringe device through the plunger rod and into the first area of the cavity during sliding movement of the plunger rod within the syringe tube.

Signed and Sealed this
Twenty-first Day of October, 2014

Michelle K. Lee
*Deputy Director of the United States Patent and Trademark Office*